United States Patent
Bustan et al.

(10) Patent No.: US 11,123,144 B2
(45) Date of Patent: Sep. 21, 2021

(54) REGISTRATION OF FRAMES OF REFERENCE

(71) Applicants: BIOSENSE WEBSTER (ISRAEL) LTD., Yokneam (IL); ACCLARENT, INC., Irvine, CA (US)

(72) Inventors: Itamar Bustan, Zichron Ya'acov (IL); Ehsan Shameli, Irvine, CA (US); Moran Levi, Tivon (IL); Itzhak Fang, Irvine, CA (US); Uriel Hod, Ein Ayala (IL); Babak Ebrahimi, Irvine, CA (US); Yoav Pinsky, Bet Keshet (IL); Fatemeh Akbarian, Irvine, CA (US); Noam Racheli, Hadera (IL)

(73) Assignees: Biosense Webster (Israel) Ltd., Yokneam (IL); Acclarent, Inc., Irvine, CA (US)

(*) Notice: Subject to any disclaimer, the term of this patent is extended or adjusted under 35 U.S.C. 154(b) by 66 days.

(21) Appl. No.: 16/748,993

(22) Filed: Jan. 22, 2020

(65) Prior Publication Data
US 2020/0242339 A1     Jul. 30, 2020

Related U.S. Application Data (60) Provisional application No. 62/797,091, filed on Jan. 25, 2019, provisional application No. 62/797,118, filed on Jan. 25, 2019.

(51) Int. Cl.
*H01F 27/28* (2006.01)
*G06K 9/00* (2006.01)
(Continued)

(52) U.S. Cl.
CPC .............. *A61B 34/32* (2016.02); *A61B 34/20* (2016.02); *G06K 9/00201* (2013.01);
(Continued)

(58) Field of Classification Search
None
See application file for complete search history.

(56) References Cited

U.S. PATENT DOCUMENTS

| 2016/0259019 A1 | 9/2016 | Gross et al. |
| 2017/0079615 A1* | 3/2017 | Burnside ............... A61B 8/4472 |
| 2018/0263725 A1 | 9/2018 | Pesach et al. |

FOREIGN PATENT DOCUMENTS

| EP | 1380266 | 1/2004 |
| EP | 3403610 | 11/2018 |

(Continued)

OTHER PUBLICATIONS

International Search Report dated Apr. 8, 2020 from corresponding PCT Application No. PCT/IB2020/050545.
(Continued)

*Primary Examiner* — Idowu O Osifade
(74) *Attorney, Agent, or Firm* — Todd J. Burns (57) ABSTRACT

Apparatus, including a patient tracker, attached to a subject, having magnetic field sensors and optical landmarks with known spatial relationships to each other. A camera acquires a 3D optical image, in a first frame of reference (FOR), of the subject's face. A magnetic radiator assembly generates magnetic fields at the subject's head, thereby defining a second FOR. A processor: processes field sensor signals to acquire location coordinates of the sensors in the second FOR; segments a tomographic image of the subject, having a third FOR, to identify the subject's face in the third FOR; computes a first transformation between the third and first FORs to map the tomographic face image to the 3D optical image; maps the optical landmarks to the third FOR; maps the respective location coordinates of the sensors to the first FOR; and computes a second transformation between the second FOR and the third FOR.

20 Claims, 6 Drawing Sheets

(51) Int. Cl.
    *A61B 34/32*    (2016.01)
    *A61B 34/20*    (2016.01)
    *G06K 9/20*    (2006.01)
    *A61B 34/30*    (2016.01)

(52) U.S. Cl.
    CPC ..... *G06K 9/00255* (2013.01); *G06K 9/00288* (2013.01); *G06K 9/209* (2013.01); *H01F 27/2804* (2013.01); *A61B 2034/2051* (2016.02); *A61B 2034/2065* (2016.02); *A61B 2034/301* (2016.02); *A61B 2034/302* (2016.02); *G06K 2209/05* (2013.01)

(56) References Cited

FOREIGN PATENT DOCUMENTS

| | | |
|---|---|---|
| GB | 2532004 | 5/2016 |
| KR | 101491922 | 2/2015 |

OTHER PUBLICATIONS

Brainlab: "Surface Matching with Z-touch and Softouch", Sep. 30, 2015, p. 1, https://www.youtube.com/watch?v=C9ngfY97Bkg.

* cited by examiner

REGISTRATION OF FRAMES OF REFERENCE

CROSS-REFERENCE TO RELATED APPLICATIONS

The present application claims the benefit of U.S. Provisional Application 62/797,091, filed 25 Jan. 2019, titled "Registration of Frames of Reference" whose disclosure is incorporated herein by reference, and also claims the benefit of U.S. Provisional Application 62/797,118, filed 25 Jan. 2019, now U.S. application Ser. No. 16/729,313 filed Dec. 28, 2019 titled "Flexible Multi-Coil Tracking Sensor" whose disclosure is incorporated herein by reference.

FIELD OF THE INVENTION

This invention relates generally to registering frames of reference of different modalities, and specifically to registering different frames of reference used in a surgical procedure.

BACKGROUND OF THE INVENTION

In an invasive surgical procedure, including a minimally invasive procedure, it is typically necessary to track an element, such as a catheter, within a patient that is not directly visible to a physician performing the procedure. Typically, a computerized tomography (CT) image, such as from fluoroscopy or magnetic resonance imaging (MRI), of the patient is available to the physician, but whatever the method used to track the element, the frame of reference of the method must be registered with the frame of reference of the image in order for the tracking to be accurate.

One method used for tracking elements within a patient is the Trudi™ electromagnetic image-guided navigation system, produced by Acclarent, Inc, of 33 Technology Drive, Irvine, Calif. 92618 USA. In this system, alternating magnetic fields are transmitted, from fixed transmitters external to the patient, so as to pass through the patient. A sensor, typically a single or multiple axis coil, is attached to the element inserted into the patient, and a processor records the currents generated by the fields traversing the sensor. The processor is able to analyze the currents so as to determine both the position and the orientation of the sensor in an electromagnetic frame of reference defined by the fixed transmitters.

SUMMARY OF THE INVENTION

An embodiment of the present invention provides apparatus, consisting of:

a patient tracker, which is configured to be attached to a head of a subject and includes one or more magnetic field sensors;

a plurality of optical landmarks having respective known spatial relationships to the one or more magnetic field sensors;

a camera configured to acquire a three-dimensional (3D) optical image, in a first frame of reference, of a face of the subject with the patient tracker attached to the head;

a magnetic radiator assembly, which generates one or more magnetic fields in a vicinity of the head of the subject, thereby defining a second frame of reference; and a processor, configured to:

receive and process signals output by the one or more magnetic field sensors in response to the one or more magnetic fields so as to acquire respective location coordinates of the magnetic field sensors in the second frame of reference, segment a tomographic image of the subject, having a third frame of reference, so as to identify the face of the subject in the third frame of reference, compute a first transformation between the third frame of reference and the first frame of reference so as to map the face in the segmented tomographic image to the 3D optical image of the face, using the first transformation, map the optical landmarks to the third frame of reference, using the known spatial relationships between the magnetic field sensors and the optical landmarks, map the respective location coordinates of the sensors to the first frame of reference, and using the mapped location coordinates and the first transformation, compute a second transformation between the second frame of reference and the third frame of reference.

In a disclosed embodiment, the patient tracker further comprises the plurality of optical landmarks of the planar tracker. That is, the optical landmarks are integral with the patient tracker.

In a disclosed embodiment the one or more magnetic field sensors and plurality of optical landmarks of the planar tracker are formed on a planar flexible sheet.

In a further disclosed embodiment the camera consists of a 3D camera using two lenses to form the 3D optical image of the face of the subject.

Alternatively, the camera consists of a 2D camera using a single lens, the apparatus further having a photo registration device to which the 2D camera is connected, and which is operative to enable the 2D camera to acquire multiple 2D images of the face of the subject. Typically, there is at least one marker configured to be attached to the face of the subject. The photo registration device may be configured to enable the 2D camera to acquire multiple 2D images of the face of the subject from respective different positions having a static orientation with respect to the face. Alternatively, the photo registration device may be configured to enable the 2D camera to acquire multiple 2D images of the face of the subject from respective different positions having different orientations with respect to the face.

In a yet further disclosed embodiment computing the first transformation includes adding an image of the patient tracker to the identified face of the subject in the third frame of reference.

In and alternative embodiment computing the first transformation includes selecting portions of the identified face of the subject in the third frame of reference that do not include a region corresponding to the patient tracker.

There is further provided, according to an embodiment of the present invention, a method, consisting of:

attaching a patient tracker to a head of a subject, the patient tracker having one or more magnetic field sensors and a plurality of optical landmarks having respective known spatial relationships to the one or more magnetic field sensors;

using a camera to acquire a three-dimensional (3D) optical image, in a first frame of reference, of a face of the subject with the patient tracker attached to the head;

generating, with a magnetic radiator assembly, one or more magnetic fields in a vicinity of the head of the subject, thereby defining a second frame of reference;

receiving and processing signals output by the one or more magnetic field sensors in response to the one or more magnetic fields so as to acquire respective location coordinates of the magnetic field sensors in the second frame of reference;

segmenting a tomographic image of the subject, having a third frame of reference, so as to identify the face of the subject in the third frame of reference;

computing a first transformation between the third frame of reference and the first frame of reference so as to map the face in the segmented tomographic image to the 3D optical image of the face;

using the first transformation, mapping the optical landmarks to the third frame of reference;

using the known spatial relationships between the magnetic field sensors and the optical landmarks, mapping the respective location coordinates of the sensors to the first frame of reference; and using the mapped location coordinates and the first transformation, computing a second transformation between the second frame of reference and the third frame of reference.

The present disclosure will be more fully understood from the following detailed description of the embodiments thereof, taken together with the drawings, in which:

DETAILED DESCRIPTION OF EMBODIMENTS

Overview

In a surgical procedure on a patient's head, such as an ENT (ear, nose and throat) procedure, an element used in the procedure may need to be tracked. To track such an element a magnetic sensor may be attached to the element, and fixed magnetic field transmitters may be placed around the head. Signals from the sensor provide the position of the element within a frame of reference of the transmitters. In order to register the transmitter frame of reference with a CT image frame of reference, present systems typically use an external sensor that may be attached to the tip of a "wand." A physician touches the wand tip on various regions of the patient's skin, such as the nose tip, a point between the eyes, and points on either sides of the eyes. While these regions are being touched a processor acquires signals from the wand sensor to find the positions of the sensor in the transmitter frame of reference. The processor correlates the found positions with the positions of the patient's skin in the CT image, so as to register the two frames of reference.

However, touching the wand sensor on the patient's skin typically causes "tenting," i.e., depression or deformation of the skin, so that the position of the wand sensor does not correspond to the position of the (untented) skin. This causes errors in the registration of the frames of reference.

For the head procedures described above, embodiments of the present invention register the electromagnetic frame with the CT frame while avoiding the problem of possible deformation of the patient's skin. In a disclosed embodiment, a registration element, herein also termed a patient tracker, which may be in the form of a planar sheet, is attached to the patient, typically to the forehead of the patient. The patient tracker comprises electromagnetic sensors as well as optical landmarks, and the sensors and landmarks are in a fixed, known, spatial relationship with respect to each other. In an alternative embodiment, rather than using a patient tracker comprising multiple sensors and landmarks, separate optical markers attached, with known spatial relationships, to respective magnetic sensors may be used.

The patient is positioned so that the fixed magnetic field transmitters surround the patient's head, and a processor acquires the signals generated by the electromagnetic sensors of the patient tracker. The processor analyzes the acquired signals to determine the positions of the electromagnetic sensors in the frame of reference of the transmitters.

A three-dimensional (3D) camera is used to capture a 3D optical image of the patient's head. The 3D image formed by the camera comprises a set of optical voxels corresponding to the face of the patient, and each voxel has three Cartesian coordinates (as well as color values). The set of optical voxels is provided to the processor.

A CT scan of the patient's head is also provided to the processor, and the processor segments the CT scan to determine CT voxels corresponding to the face of the patient. The processor correlates the CT voxels with the optical voxels from the 3D camera image, so as to register the 3D optical image frame of reference with the CT frame of reference.

Within the 3D optical image is an image of the patient tracker, including optical images of the landmarks of the tracker. Since the spatial relationship of the landmarks to the electromagnetic sensors is known, the processor is able to use this relationship to register the 3D optical image frame of reference with the frame of reference of the magnetic field transmitters.

The processor then combines the two registrations, i.e., the 3D optical image frame of reference with the CT frame of reference, and the 3D optical image frame of reference with the frame of reference of the magnetic field transmitters, to form a registration of the CT frame of reference with the frame of reference of the magnetic field transmitters.

DETAILED DESCRIPTION

Figure 1:
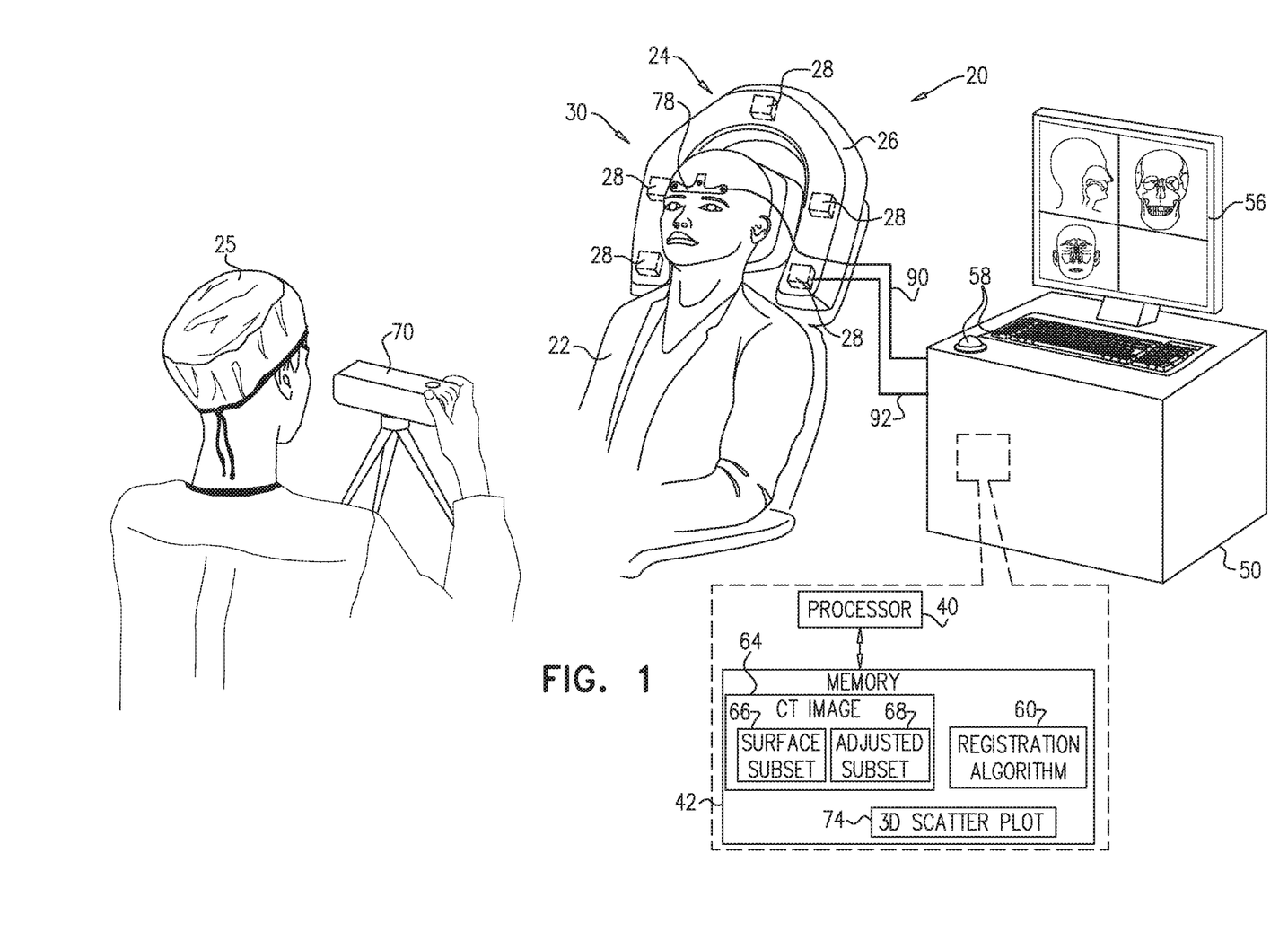
FIG. 1 is a schematic illustration of a registration system, according to an embodiment of the present invention.

Reference is now made to FIG. 1, which is a schematic illustration of a registration system 20, according to an embodiment of the present invention. In the following description, system 20 is assumed to be used to register two frames of reference used on a patient 22, prior to the patient undergoing an invasive medical procedure. By way of example, in the description herein patient 22 is assumed to be seated in a chair, such as may be the case for certain ENT (ear, nose and throat) procedures. However, embodiments of the present invention are not limited to a patient being in a particular position, so that patient 22 may be located in any convenient position, for example on a bed.

The medical procedure undergone by the patient is assumed to comprise tracking of an object, such as a catheter, which is inserted into the patient by a medical professional 25. The tracking is provided by a magnetic tracking system 24, described in more detail below.

The magnetic tracking system comprises a magnetic radiator assembly 26 which is positioned around the patient's head. Assembly 26 comprises magnetic field radiators 28 which are fixed in position and which transmit alternating sinusoidal magnetic fields into a region 30 wherein the head of patient 22 is located. By way of example, radiators 26 of assembly 24 are arranged in an approximately horseshoe shape around the head of patient 22. However, alternate configurations for the radiators of assembly 26 will be apparent to those having ordinary skill in the art, and all such configurations are assumed to be comprised within the scope of the present invention.

A magnetic sensor, herein assumed to comprise a coil, is attached to the object being tracked within patient 22. The attached coil generates electrical signals in response to the alternating magnetic fields traversing the coil, and these signals are transferred to a system processor 40. The processor is configured to process the signals so as to derive location and orientation values for the sensor. Other elements of system 20, including radiators 28, are controlled by system processor 40.

The TruDi system referred to above uses a tracking system similar to that described herein for finding the location and orientation of a coil in a region irradiated by magnetic fields.

Processor 40 uses software stored in a memory 42 to operate system 20. The software may be downloaded to processor 40 in electronic form, over a network, for example, or it may, alternatively or additionally, be provided and/or stored on non-transitory tangible media, such as magnetic, optical, or electronic memory. Processor 40 uses the software, inter alia, to analyze the signals received from the magnetic sensor. Software for a registration algorithm 60, comprising steps executed by the processor in implementing registration system 20, is also stored in memory 42. Registration algorithm 60 is described in more detail below.

Processor 40 may be mounted in a console 50, which comprises operating controls 58 that typically include a keypad and/or a pointing device such as a mouse or trackball. Console 50 connects to the radiators via a cable 92 and/or wirelessly. Professional 25 may use operating controls 58 to interact with the processor while performing the medical procedure referred to above. While performing the procedure, the processor may present results of the procedure on a screen 56.

As described above magnetic tracking system 24 is able to track the position and orientation of a magnetic sensor in region 30, by virtue of the magnetic fields transmitted into the region from radiators 28. It will be understood that the position and orientation derived for system 24 is with reference to a frame of reference (FOR) of the magnetic system, as defined by the positions of radiators 28. However, in order for the tracking of the sensor to be useful, the magnetic system FOR needs to be registered with the FOR of an image of patient 22. In the following description algorithm 60 of system 20 is assumed to be used to register the FOR of magnetic tracking system 24 with the FOR of a CT (computerized tomography) image 64 of patient 22 that is stored in memory 42. Subsets 66 and 68 of image 64, described further below, are also stored in memory 42.

While the CT image may typically comprise a magnetic resonance imaging (MRI) image or a fluoroscopic image, in the description herein the image is assumed to comprise, by way of example, a fluoroscopic CT image.

As is described in more detail below, professional 25 uses a 3D (three-dimensional) camera 70 to capture a 3D optical image of the face of patient 22. In one embodiment camera 70 is a RealSense 3D camera, produced by Intel Corporation of Santa Clara, Calif. The 3D camera typically uses two lenses. The 3D optical image comprises a set of optical voxels, each voxel having three Cartesian coordinates as well as color, typically RGB (red, green, blue) values. The set of optical voxels is herein also termed a 3D scatter plot 74, and the optical voxels of scatter plot 74 are stored in memory 42.

For the registration implemented by system 20, a patient tracker 78 is positioned on patient 22. Patient tracker 78 is described with reference to FIGS. 6A and 6B below.

Figure 2:
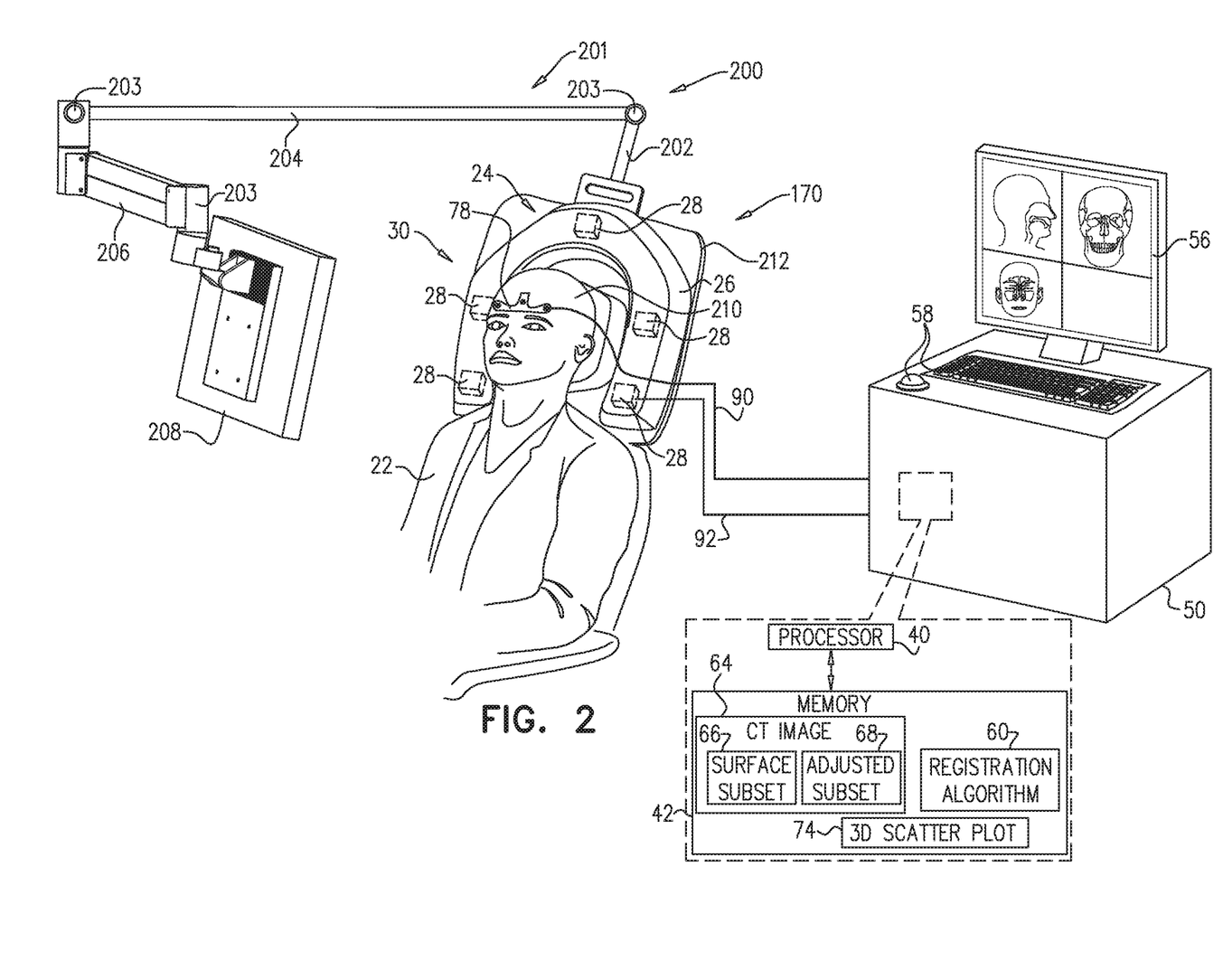
FIG. 2 is a schematic illustration of a registration system, according to an alternative embodiment of the present invention.

FIG. 2 is a schematic illustration of a registration system 170, according to an alternative embodiment of the present invention. Apart from the differences described below, the operation of system 170 is generally similar to that of system 20 (FIG. 1), and elements indicated by the same reference numerals in both systems are generally similar in function. In place of camera 70 of system 20, system 170 comprises a photo registration device 200, which may be used to capture multiple images of a patient's face or other surgical site from different position and orientations, and may combine those multiple images into a set of 3D modeling data with depth (e.g., a 3D model, a point cloud, a depth map, etc.)

Photo registration device 200 includes an arm 201 with a number of articulated support members. Arm 201 shown in FIG. 2 includes a vertical extension member 202, a horizontal extension member 204, and a positioning member 206 that are interconnected by a set of joints 203 (e.g., swivel joints, ball joints, hinge joints, or other joints allowing rotation around one or more axis). Joints 203 may be manually articulable, or may be automated such that each joint 203 may be independently rotated based upon control signals from a device such as processor 40 or a dedicated processor of photo registration device 200. In some implementations where joints 203 allow for manual positioning, the joints may support a wide range of movement, but may be adapted to only lock or immobilize when in certain positions. This may be advantageous where only a small number of images may be needed from predetermined positions, as a user could manually manipulate arm 201 until each of joints 203 reaches the desired position and locks until a release mechanism such as a pin or button is operated to release the joint.

Vertical extension member 202 is positioned proximately to a headrest 212 of the patient chair, and may be rotated (e.g., rolled around its vertical axis) to rotate arm 201 about head 210 of patient 22. Vertical extension member 202 may be manually rotated or may be automatically rotated similar to joints 203, such as by a control signal from processor 40 or another device. Positioning member 206 is connected to a camera 208 by a joint 203, and may be rotated to position the camera as desired relative to patient head 210. By rotating vertical extension member 202 around its vertical axis, and rotating horizontal extension member 204, positioning member 206, and camera 208 around joints 203, the camera can be positioned in a wide range of locations while being oriented towards head 210.

Camera 208 itself is a two-dimensional (2D) camera, i.e., a camera that uses a single lens to acquire 2D images of scenes observed by the camera. Camera 208 may be an integrated component of arm 201, such as a digital imaging device that is permanently joined with a joint 203, or it may be a digital imaging device or other device with digital imaging capabilities that is placed in a holder that itself is coupled with the joint. As an example, camera 208 could be a handheld digital camera, a smartphone including a digital camera, or a tablet including a digital camera, that may be placed into a holder that isolates its movement and allows it to be rotated around a joint 203 when in place. In such an implementation, camera 208 itself may produce control signals to control joints 203 of arm 201 and the rotation of vertical extension member 202.

As an example, where camera 208 is a smartphone, the smartphone may be configured with a software application that connects the smartphone to a control device (not pictured) of arm 201 via Bluetooth, Wi-Fi, or other communication means, and produces a set of control signals to automatically orient the camera towards patient head 210 while capturing images at a plurality of positions (e.g., a 180 degree rotation around patient head 210 from below, from above, and from an equal height). Alternately, where camera 208 is a smartphone or tablet, it may similarly connect to processor 40, which itself provides control signals to arm 201 and receives images captured by the camera at various positions. As another example, where camera 208 is a permanently integrated digital camera, it may be coupled with processor 40 or another device wirelessly or via a physical connection such as a data cable running through arm 201 and may provide captured image data via that connection.

Camera 208 capabilities may vary by implementation, but may include for example high resolution photo and video, image stabilization, high speed image capture, infrared light projection and capture, light projection, local storage of images, transmission of images via a wireless communication device, an internal battery, and other features. Other variations of camera 208 exist and will be apparent to one of ordinary skill in the art in light of this disclosure.

Figure 3A:
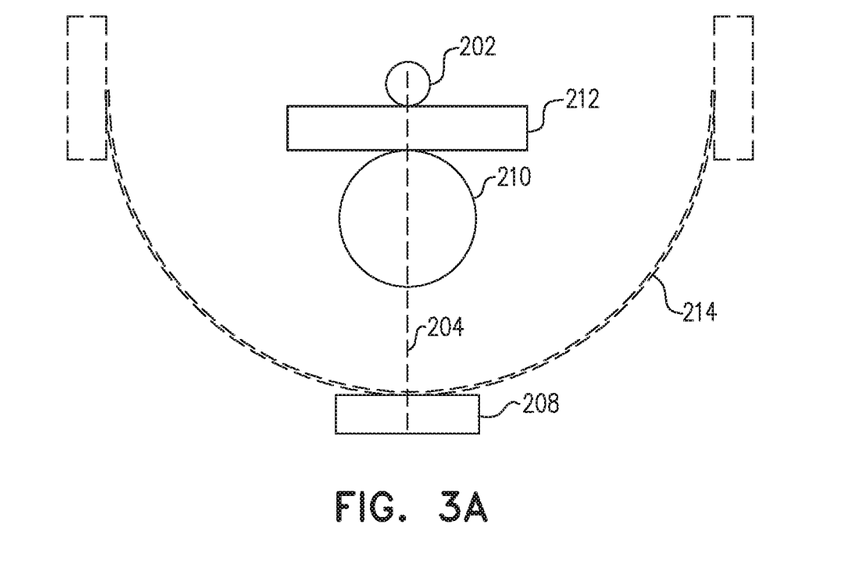
FIGS. 3A and 3B depict schematic views of a rotation or orbital path, according to an embodiment of the present invention.
Figure 3B:
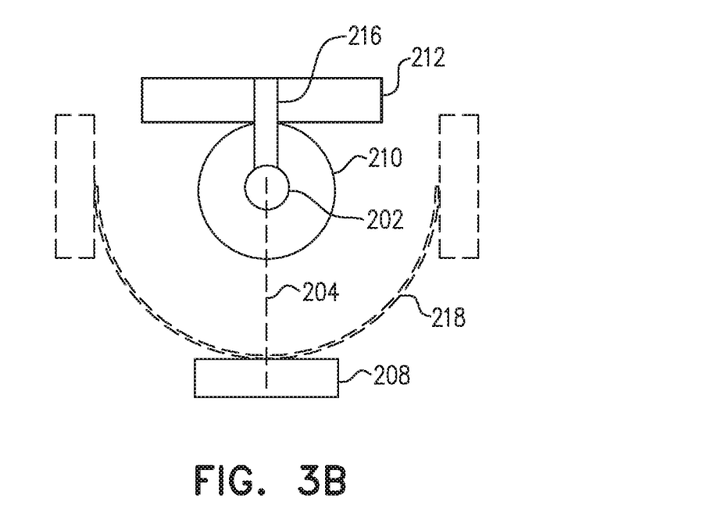

FIGS. 3A and 3B depict schematic views of a rotation or orbital path of photo registration device 200 of FIG. 2 around patient head 210, according to an embodiment of the present invention. As shown in FIG. 3A, vertical extension member 202 is mounted just behind headrest 212, and when rotated will rotate horizontal extension member 204 around patient head 210. With vertical extension member 202 as a rotational axis, camera 208 may rotate or orbit around a path 214 while capturing images of patient head 210 from different positions around the path. The camera orientation may remain static through path 214, which will result in a series of images of patient head 210 with varying relative orientations, since the rotational axis, vertical extension member 202, is offset from the target, patient head 210, and so the relative orientation of camera 208 to head 210 will change throughout path 214. Alternatively, camera 208 may be repositioned by its joint 203 while rotating or orbiting throughout path 214 in order to maintain a static orientation relative to head 210, in order to generate a series of images of the patient head from a static orientation around the path. While a static orientation relative to patient head 210 is not required to combine a set of images into 3D data, it may, in some implementations, improve the speed and accuracy at which such 3D data is produced.

As an example of another implementation which provides image sets with a static relative orientation to patient head 210, FIG. 3B depicts a schematic view of an alternate rotation or orbit path of the photo registration device of FIG. 2. In FIG. 3B, it can be seen that a centering member 216 extends outwards from headrest 212 and centers vertical extension member 202 over patient head 210. In effect, this shifts the rotational axis of arm 201, so that vertical extension member 202 is now substantially centered above patient head 210 rather than being offset as in FIG. 3A. As a result, a rotational or orbital path 218 traveled by camera 208 is of a shorter length (i.e., the circumferential path traveled is shorter), the distance between camera 208 and patient head 210 is reduced (i.e., the radius from the rotational axis), resulting in more detailed images, and a static orientation of camera 208 relative to the patient head 210 is maintained throughout.

Figure 4A:
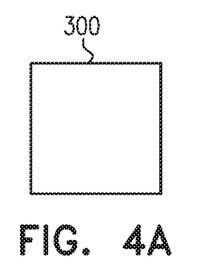
FIGS. 4A-4C depict exemplary markers, according to an embodiment of the present invention.
Figure 4B:
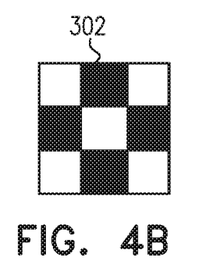
Figure 4C:
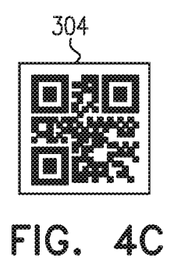
Figure 5:
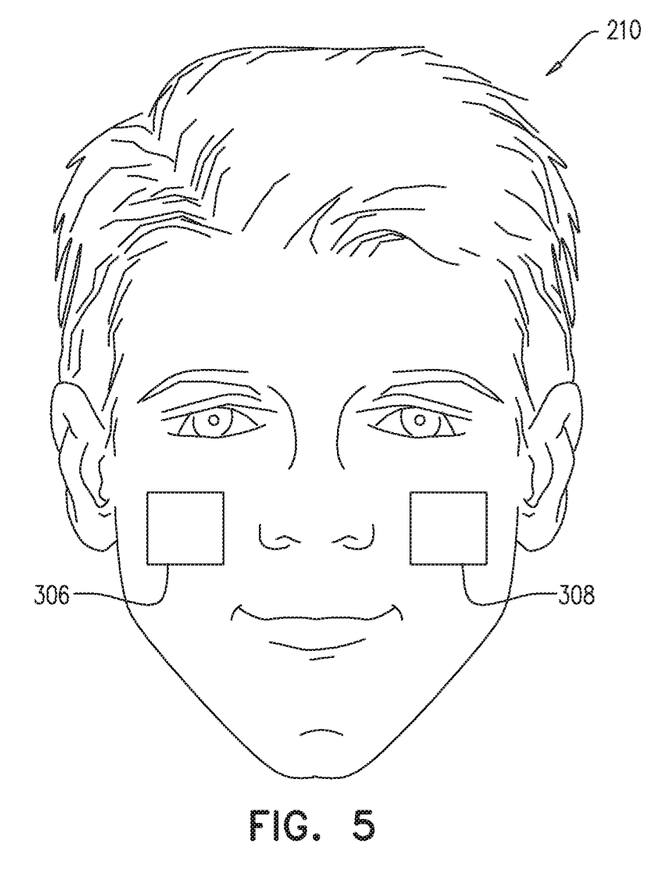
FIG. 5 is a schematic diagram of a patient head upon which the markers of FIGS. 4A-4C may be placed, according to an embodiment of the present invention.

FIGS. 4A-4C depict exemplary markers, and FIG. 5 is a schematic diagram of a patient head upon which the markers may be placed, according to an embodiment of the present invention. The markers are usable with photo registration device 200 of FIG. 2, which may be placed on patient head 210 as shown in FIG. 5 to aid in production of 3D image data from captured images. FIG. 4A shows a reflective marker 300 having an adhesive back surface and a reflective front surface. The front surface of reflective marker 300 may be, for example, a glossy or dull surface, having a color or other reflective characteristic that enables the reflective marker) to be identified within an image using an image analysis or object recognition technique. As an example, reflective marker 300 may be a sticker having a silver or mirrored front surface, a bright white front surface, or a high contrast colored surface such as a bright yellow, green, or red. When placed on a patient's face such as shown in FIG. 5, reflective marker 300 will be sharply contrasted against the patient's skin in digital images, allowing the position, size, outline, shape, and other characteristics of the reflective marker (300) to be more easily identified by object recognition techniques applied to the image.

FIG. 4B shows a patterned marker 302, which may be used similarly as reflective marker 300 and placed on a patient's face in order to provide high contrast, easily identifiable objects for photo recognition. Patterned marker 302 may have both highly reflective portions on the front surface (e.g., such as white squares of the checkerboard pattern) as well as low or lower reflective portions on the front surface (e.g., such as the black squares of the checkerboard pattern). Each of the placed patterned markers 302 may have the same or a different pattern, in varying implementations. For example, in some implementations patterned marker 302 may have a pattern that both allows the marker to be more easily identified within an image, and also identifies the position of that marker on the patient face, such as where a marker placed at a first position 308 in FIG. 5 may have a pattern associated with "left cheek", while a marker placed at a second position 306 may have a pattern associated with "right cheek". FIG. 6C shows a coded marker 304 which may be, for example, a QR code, barcode, or other optically encoded pattern. Coded marker 304 may be used similarly to patterned marker 302.

By placing one or markers on the patient face, as shown in FIG. 5, production of 3D image data from 2D image data may be improved. For example, the presence of markers within an image can be used to determine the scale of the image, which may include the depth of the captured objects, since a marker such as reflective marker 300 has a known size (e.g., one square inch). The known size of the marker can be associated with a number of imaged pixels at various depths (e.g., a one-inch length of marker imaged from a twelve-inch depth is captured as 300 pixels, while the same marker length imaged from a six-inch depth is captured as 600 pixels). Thus, by identifying the position and pixel size of the marker within the image data, a depth or distance to the imaged object can be determined, as well as other distances associated with the image.

The presence of a marker within the image having a known shape (e.g., a square) can be used to determine an orientation of the image capture device to the surface on which the marker is placed. When a square marker placed on a surface is captured by an imaging device oriented directly at the marker, it will appear as a square in captured images. When captured from offset orientations however, the square marker may instead appear as a non-square quadrilateral having a shape and other characteristics determined by the orientation of the image capture device relative to the square marker. With a known actual shape, and a predictable change in visual appearance dependent upon orientation, the visual appearance of a square marker identified within a 2D object can be used to determine the orientation of the imaging device relative to the marker. The orientation of the imaging device to the marker can then be used for multiple 2D images to relate them to each other in 3D space.

Figure 6A:
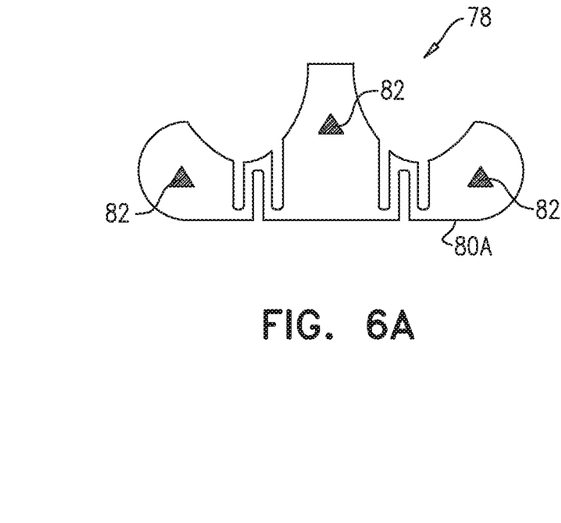
FIGS. 6A and 6B are schematic figures illustrating a patient tracker used in the systems of FIG. 1 and FIG. 2, according to an embodiment of the present invention.
Figure 6B:
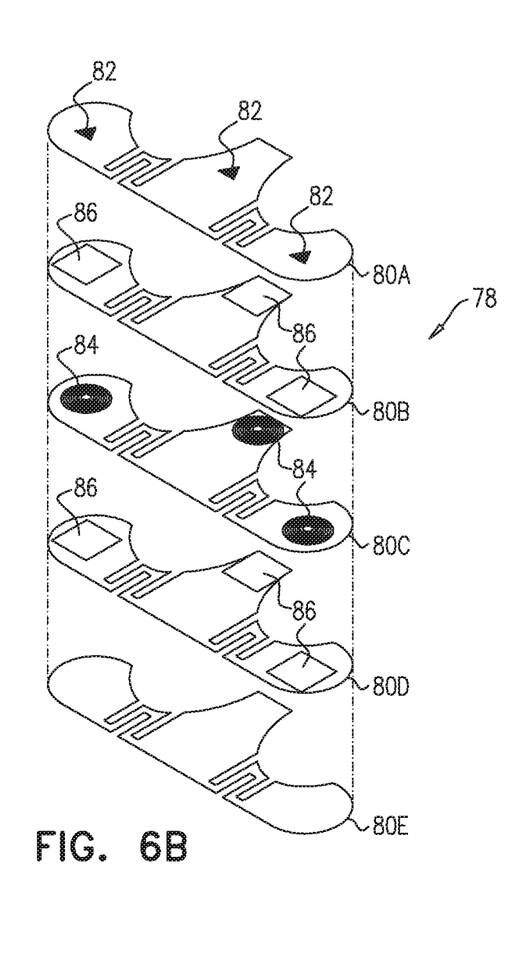

FIGS. 6A and 6B are schematic figures illustrating patient tracker 78, according to an embodiment of the present invention. Patient tracker 78 is formed as a substantially planar sheet, and FIG. 6A illustrates a view of the tracker, as seen by camera 70 or camera 208, i.e. after the tracker has been positioned on patient 22. FIG. 6B is an exploded view of the tracker.

In one embodiment tracker 78 is constructed of five laminar sheets 80A, 80B, 80C, 80D, and 80E, all sheets having substantially the same shape, and being bonded together. Sheet 80A is an upper sheet, also shown in FIG. 2A, and incorporated in the sheet is a plurality of optically identifiable landmarks 82. Herein by way of example sheet 80A comprises three optical landmarks 82, but other embodiments may comprise other numbers of landmarks. As described above, in an alternative embodiment, rather than using a patient tracker comprising multiple sensors and landmarks, separate optical markers (i.e., landmarks) attached, with known spatial relationships, to respective magnetic sensors may be used. In a preferred embodiment, the optical markers are an integral part of the patient tracker as described herein.

Sheet 80C is an intermediary laminar sheet, typically formed from a flexible insulating material, upon which are formed, typically by printing, planar conducting coils 84 in the form of conductive spirals. Coils 84 act as electromagnetic sensors. There are the same number of coils 84 as landmarks 82, and each coil is located on sheet 80C so that it is in a known spatial relationship with a respective landmark 82. Herein, by way of example, each coil 84 is located to be directly aligned with a respective landmark 82 when the sheets of the tracker are bonded together. However, other embodiments may be formed with different known spatial relationships between the coils and the landmarks. For example, coils and landmarks may be offset by known spatial amounts.

A cable 90 (FIGS. 1 and 2) connects coils 84 to processor 40, but for simplicity connections of coils 84 to the cable are not shown in FIG. 6A or 6B.

Sheet 80E is a lower laminar sheet formed from biocompatible adhesive, and it is this sheet that contacts patient 22 during operation of system 20.

Sheets 80B and 80D are intermediate laminar sheets, formed of conductive material, so as to act as electrical shields for coils 84. Within sheets 80B are non-conductive regions 86, typically openings, aligned with coils 84, the presence of the non-conductive regions enabling the coils to operate correctly.

Figure 7:
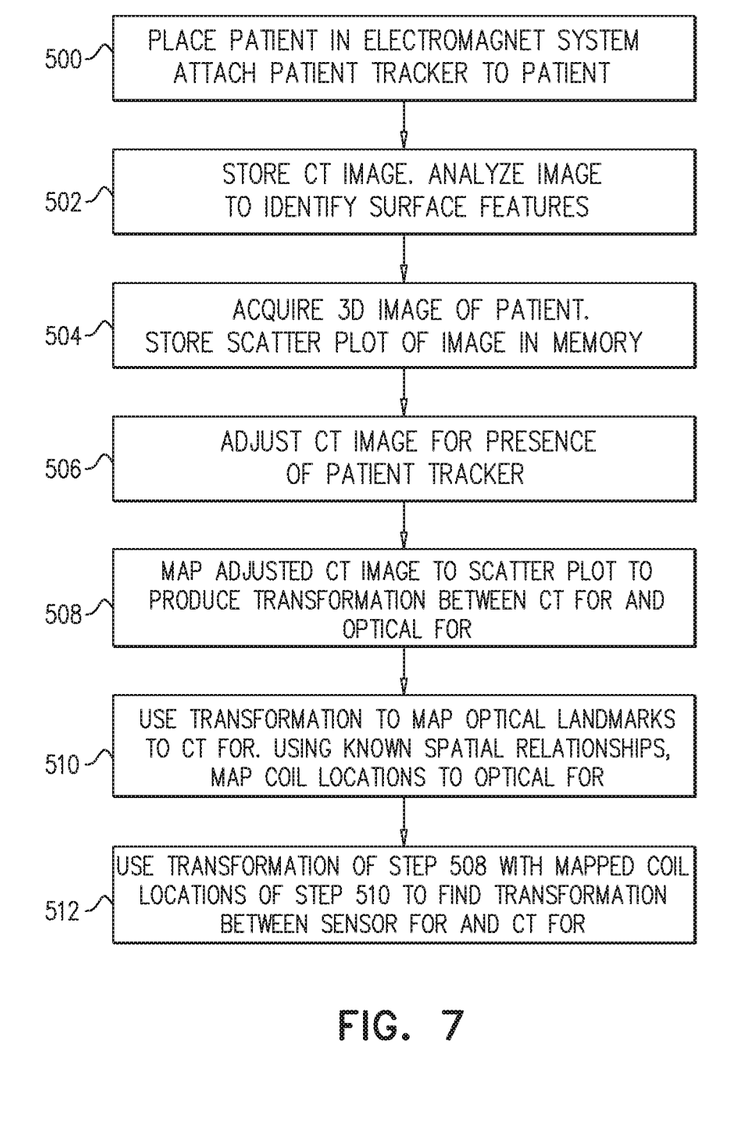
FIG. 7 is a flowchart of steps in executing an algorithm, according to an embodiment of the present invention.

FIG. 7 is a flowchart of steps performed by processor 40 and professional 25 in executing algorithm 60, according to an embodiment of the present invention. The flowchart description assumes that registration system 20 is used, but the description may be altered, mutatis mutandis, if registration system 170 is used.

In an initial step 500 magnetic tracking system 24 is activated, and the head of patient 22 is placed within region of the system. Patient tracker 78 is attached to the forehead of the patient, using biocompatible adhesive sheet 80E, and so that optical landmarks 82 are uppermost and are visible. Cable 90 is connected between the patient tracker and processor 40, and the processor may be activated to acquire signals conveyed by the cable from coils 84. The processor analyzes the signals to calculate the positions of the coils in the frame of reference defined by magnetic transmitters 28. If the calculated positions are found to be within an expected part of region 30, processor 40 may provide an indication that the magnetic tracking system is operating correctly to professional 25, for example by placing a notice on screen 56.

In a CT image step 502, a CT image of the head of patient 22 is stored in memory 42. Processor 40 segments the image to identify a subset of CT voxels of the stored image corresponding to surface features of the face of the patient, and the subset is stored as surface subset 66.

In an optical image acquisition step 504, professional 25 activates camera 70 to acquire a 3D optical image of the face of patient 22, and the acquired image is stored as scatter plot 74 in memory 42. It will be understood that the image acquired by camera 70 includes an image of patient tracker 78 that is on the face of the patient.

Embodiments of the present invention use any suitable algorithm, such as the Iterative Closest Point (ICP) algorithm, to find the transformation that best maps surface subset of CT voxels 66 to the optical voxels of 3D scatter plot 74. However, up to step 504 there is a known difference in the two sets of voxels, since an image of the patient tracker is present in scatter plot 74 but is not present in CT voxel subset 66.

In an adjustment step 106 the absence of an image of the patient tracker in CT voxel subset 66 is compensated for by adding an image of the patient tracker to the CT voxel subset. The addition may be implemented by presenting an image of the CT voxel subset to professional 25 on screen 56, allowing the professional to overlay an image of the patient tracker on the presented image, and storing the combined image as an adjusted CT voxel subset 68.

Alternatively in step 506, adjusted subset 68 is derived from CT voxel subset 66 by professional 25 selecting portions of subset 66 that do not include a region corresponding to the patient tracker image. Professional 25 may perform the selection on an image of subset 66 presented on screen 56, and the selected portions are stored as adjusted CT voxel subset 68.

In a mapping step 508, processor 40 maps adjusted CT voxel subset 68 to the voxels of scatter plot 74. If in step 106 the adjusted CT subset includes an image of the patient tracker, then the mapping is performed for all the voxels of the two sets. Alternatively, if step 506 is implemented by selecting portions of subset 66 that do not include the patient tracker image, processor 40 makes a corresponding selection in the voxels of scatter plot 74, and the mapping is performed between the selected sets of voxels.

The mapping provides a registration between the FOR of the CT image of patient 22 and the FOR of the optical image of the patient. Processor 40 may quantify the registration as a first transformation matrix M[CT-OPT] which may be used to transform entities in one of the frames of reference to the other frame of reference.

In a further registration step 510, using the first transformation, the processor maps optical landmarks 82 to the CT image FOR. Processor 40 then uses the known spatial relationship between optical landmarks 82 and coils 84 to perform a mapping of the locations of the coils to the FOR of the optical image.

In a final registration step 512, processor 40 uses the first transformation produced in step 508, and the mapped locations produced in step 510, to produce a registration between the FOR of the magnetic tracking system and the FOR of the CT image. The resulting registration may be quantified as a second transformation matrix M[CT-MAGN].

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus, comprising: a patient tracker, which is configured to be attached to a head of a subject and comprises one or more magnetic field sensors; a plurality of optical landmarks having respective known spatial relationships to the one or more magnetic field sensors; a camera configured to acquire a three-dimensional (3D) optical image, in a first frame of reference, of a face of the subject with the patient tracker attached to the head; a magnetic radiator assembly, which generates one or more magnetic fields in a vicinity of the head of the subject, thereby defining a second frame of reference; and a processor, configured to: receive and process signals output by the one or more magnetic field sensors in response to the one or more magnetic fields so as to acquire respective location coordinates of the magnetic field sensors in the second frame of reference, segment a tomographic image of the subject, having a third frame of reference, so as to identify the face of the subject in the third frame of reference, compute a first transformation between the third frame of reference and the first frame of reference so as to map the face in the segmented tomographic image to the 3D optical image of the face, using the first transformation, map the optical landmarks to the third frame of reference, using the known spatial relationships between the magnetic field sensors and the optical landmarks, map the respective location coordinates of the magnetic field sensors to the first frame of reference, and using the mapped location coordinates and the first transformation, compute a second transformation between the second frame of reference and the third frame of reference.

2. The apparatus according to claim 1, wherein the patient tracker further comprises the plurality of optical landmarks.

3. The apparatus according to claim 2, wherein the one or more magnetic field sensors and plurality of optical landmarks of the planar tracker are formed on a planar flexible sheet.

4. The apparatus according to claim 1, wherein the camera comprises a 3D camera using two lenses to form the 3D optical image of the face of the subject.

5. The apparatus according to claim 1, wherein the camera comprises a 2D camera using a single lens, the apparatus further comprising a photo registration device to which the 2D camera is connected, and which is operative to enable the 2D camera to acquire multiple 2D images of the face of the subject.

6. The apparatus according to claim 5, and comprising at least one marker configured to be attached to the face of the subject.

7. The apparatus according to claim 5, wherein the photo registration device is configured to enable the 2D camera to acquire multiple 2D images of the face of the subject from respective different positions having a static orientation with respect to the face.

8. The apparatus according to claim 5, wherein the photo registration device is configured to enable the 2D camera to acquire multiple 2D images of the face of the subject from respective different positions having different orientations with respect to the face.

9. The apparatus according to claim 1, wherein computing the first transformation comprises adding an image of the patient tracker to the identified face of the subject in the third frame of reference.

10. The apparatus according to claim 1, wherein computing the first transformation comprises selecting portions of the identified face of the subject in the third frame of reference that do not include a region corresponding to the patient tracker.

11. A method, comprising: attaching a patient tracker to a head of a subject, the patient tracker comprising one or more magnetic field sensors; attaching a plurality of optical landmarks having respective known spatial relationships to the one or more magnetic field sensors; using a camera to acquire a three-dimensional (3D) optical image, in a first frame of reference, of a face of the subject with the patient tracker attached to the head; generating, with a magnetic radiator assembly, one or more magnetic fields in a vicinity of the head of the subject, thereby defining a second frame of reference; receiving and processing signals output by the one or more magnetic field sensors in response to the one or more magnetic fields so as to acquire respective location coordinates of the magnetic field sensors in the second frame of reference; segmenting a tomographic image of the subject, having a third frame of reference, so as to identify the face of the subject in the third frame of reference; computing a first transformation between the third frame of reference and the first frame of reference so as to map the face in the segmented tomographic image to the 3D optical image of the face; using the first transformation, mapping the optical landmarks to the third frame of reference; using the known spatial relationships between the magnetic field sensors and the optical landmarks, mapping the respective location coordinates of the magnetic field sensors to the first frame of reference; and using the mapped location coordinates and the first transformation, computing a second transformation between the second frame of reference and the third frame of reference.

12. The method according to claim 11, wherein the patient tracker further comprises the plurality of optical landmarks of the planar tracker.

13. The method according to claim 12, wherein the one or more magnetic field sensors and plurality of optical landmarks of the planar tracker are formed on a planar flexible sheet.

14. The method according to claim 11, wherein the camera comprises a 3D camera using two lenses to form the 3D optical image of the face of the subject.

15. The method according to claim 11, wherein the camera comprises a 2D camera using a single lens, the method further comprising connecting a photo registration device to the 2D camera, the device being operative to enable the 2D camera to acquire multiple 2D images of the face of the subject.

16. The method according to claim 15, and comprising attaching at least one marker to the face of the subject.

17. The method according to claim 15, wherein the photo registration device is configured to enable the 2D camera to acquire multiple 2D images of the face of the subject from respective different positions having a static orientation with respect to the face.

18. The method according to claim 15, wherein the photo registration device is configured to enable the 2D camera to acquire multiple 2D images of the face of the subject from respective different positions having different orientations with respect to the face.

19. The method according to claim 11, wherein computing the first transformation comprises adding an image of the patient tracker to the identified face of the subject in the third frame of reference.

20. The method according to claim 11, wherein computing the first transformation comprises selecting portions of the identified face of the subject in the third frame of reference that do not include a region corresponding to the patient tracker.

* * * * *